(12) United States Patent
Ariza

(10) Patent No.: US 8,105,256 B1
(45) Date of Patent: Jan. 31, 2012

(54) POST OPERATIVE PRESSURE GARMENT

(76) Inventor: Alfredo Ernesto Hoyos Ariza, Miami, FL (US)

(*) Notice: Subject to any disclaimer, the term of this patent is extended or adjusted under 35 U.S.C. 154(b) by 33 days.

(21) Appl. No.: 12/287,817

(22) Filed: Oct. 14, 2008

(51) Int. Cl.
*A61F 5/00* (2006.01)

(52) U.S. Cl. .......................................................... 602/19

(58) Field of Classification Search .................. 602/4–5, 602/19, 20–23, 26–27, 60–62, 75; 128/856
See application file for complete search history.

(56) References Cited

U.S. PATENT DOCUMENTS

| | | | | | |
|---|---|---|---|---|---|
| 2,505,720 | A | * | 4/1950 | Cooper-Smith et al. ...... | 128/889 |
| 5,158,531 | A | * | 10/1992 | Zamosky ........................ | 602/19 |
| 5,718,670 | A | * | 2/1998 | Bremer ........................... | 602/19 |
| 5,823,984 | A | * | 10/1998 | Silverberg ...................... | 602/61 |
| 6,585,673 | B1 | * | 7/2003 | Bass ............................... | 602/60 |
| 2002/0106970 | A1 | * | 8/2002 | Falla ............................... | 450/1 |

* cited by examiner

*Primary Examiner* — Michael A. Brown
(74) *Attorney, Agent, or Firm* — Malloy & Malloy, P.A.

(57) ABSTRACT

A compression garment for treating post operative patients involved in body contouring surgery and structured for removable disposition in an operative position about the torso or other predetermined portion of the patient's body. The compression garment is dimensioned, configured and structured to apply a predetermined, appropriate compression to the surgically affected portions of the patient in order to reduce pain, diminish swelling and avoid fluid accumulation, while not impairing the venous and lymphatic circulation of the affected body portion. The garment includes a base of flexible, compressible material having at least one, but more practically both a first and second cover member overlying the internal and external surfaces of the base, wherein a closure assembly serves to removably maintain the garment in a variably closed orientation while in the operative position such that appropriate compressive force is applied to the affected areas including adjacent soft tissue and bony prominences.

11 Claims, 2 Drawing Sheets

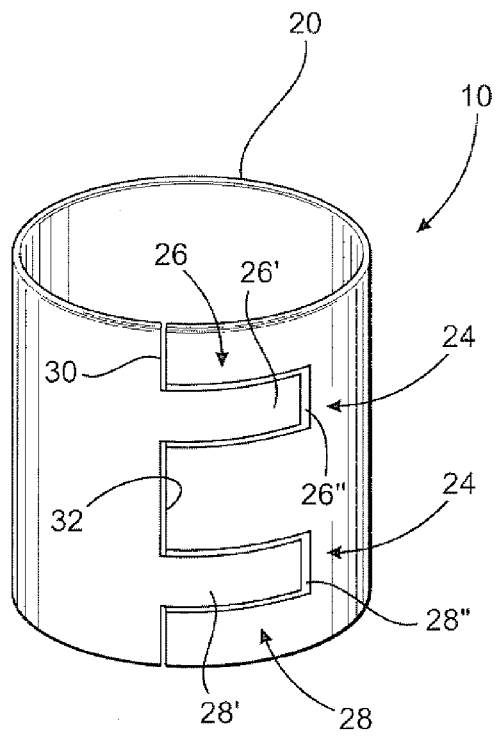
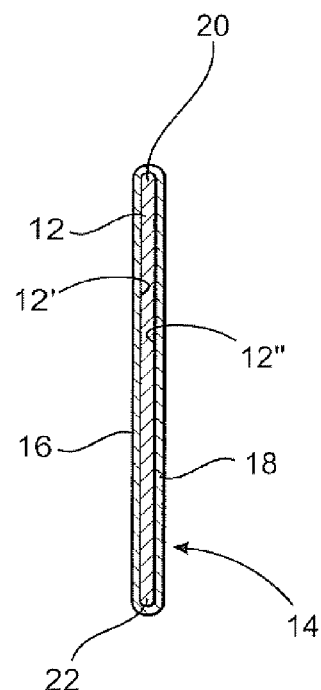
FIG. 1
FIG. 3
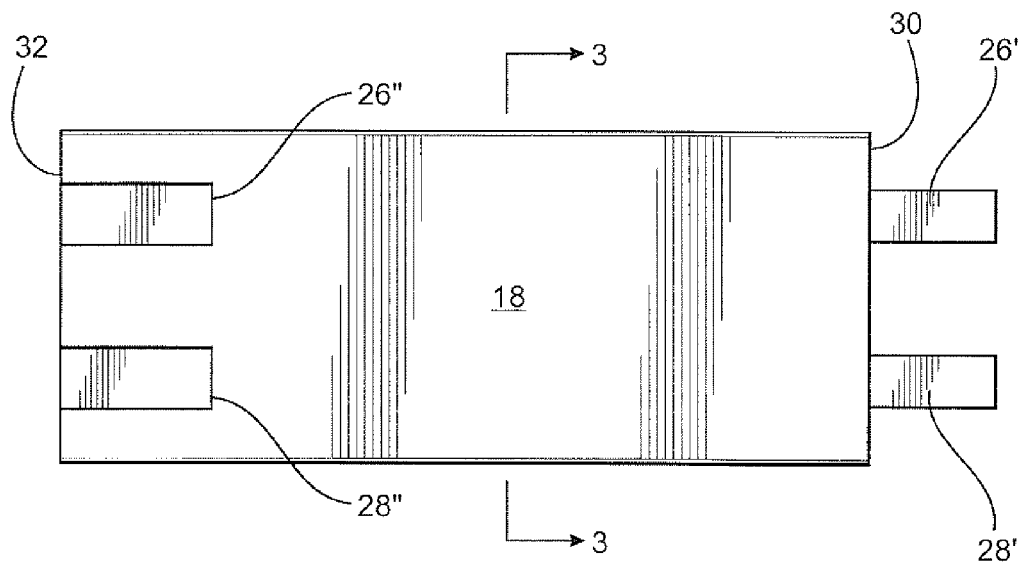
FIG. 2

POST OPERATIVE PRESSURE GARMENT

BACKGROUND OF THE INVENTION

1. Field of the Invention

The present invention is directed to a compression garment removably disposed on a post operative patient involved in body sculpting surgery. The compression garment is dimensioned and configured to assume an operative position and as such exert a predetermined, appropriate amount of compression on surgically affected portions including both the soft tissue and bony prominences of the patient's body in order to reduce pain, diminish swelling and avoid fluid accumulation.

2. Description of the Related Art

Lipoplasty or other body contouring surgery procedures has become increasingly popular and is commonly practiced in many medically advanced countries throughout the world. Subsequent to undergoing such surgical procedures, the patient frequently encounters pain, a relatively extended healing period due to swelling and the accumulation of fluids, commonly referred to as "seroma". In order to avoid or at least significantly reduce these problems, the patient is at least generally treated by subjecting the surgically affected areas of the body by the application of compressive forces. Typically, such compression must generally be less than 10 mm/hg. Compressive forces in this range are generally considered sufficient to reduce symptoms of the type set forth above but not enough to impair venous and/or lymphatic circulation.

However, conventionally available means to apply such compressive forces fail to consider the variations in the patient's body, such as, but not limited to the "bony areas or prominences" such as, but not limited to the iliac crest and/or the rib cage area. These areas of bony prominences, when subjected to the same compressive force as the soft tissue areas, are frequently subjected to abrasions and other injuries due to excessively high pressure being applied to these bony portions. In contrast, soft tissue portions of the patient's body, including the central part of the abdomen, are generally subjected to lower and sometimes inadequate compressive forces. This is due to a "tent" effect at least partially caused by the adjacent or surrounding bony prominences engaging the force generating structure applied to the patient's body. Accordingly, certain portions of the patient's body are under a lower compression and are accordingly more prone to develop complications, such as fluid retention and fibrosis.

Therefore there is a need in the medical profession for a device or assembly which is properly structured, dimensioned and configured to apply an appropriate compressive force to surgically treated portions of the patient's body. Such a proposed device should be applied during a post operative period so as to alleviate and/or significantly reduce discomfort to the patient by the reduction of pain, the diminishing of swelling and/or the avoidance of fluid accumulation, as generally set forth above. Further, such a proposed and preferred compressive generating device could, in at least one embodiment, comprise a compression garment secured in an appropriate closed orientation about the surgically treated portion of the patient's body in a manner which facilitates the application of the appropriate compressive forces. In addition, the structure of such a preferred compression garment should be such as to decrease the compressive forces applied to or in the area of the bony prominences, while increasing or applying the appropriate pressure on the soft tissue areas. The preferred compression garment would thereby prevent or reduce discomfort to the bony prominences while increasing the comfort and avoiding complications to the overall surgical site of the lipoplasty or other body contouring surgery.

Further, due to the advancement in body contouring surgical procedures, the surgically affected areas of the patient's body may involve a majority or substantial portion of the torso of the patient. As such, a preferred and proposed compression garment may preferably assume and be mounted on a post operative patient in a preferred operative position which may comprise, in certain applications, the surrounding of the entire torso area of the patient. Accordingly, when assuming such an operative position the compression garment is disposed in a closed orientation which is variable at least to the extent of accommodating patients of different sizes. However, an appropriate compressive force will be applied in surrounding relation to appropriate portions of the torso of the post operative patient.

Finally, the preferred and proposed compression garment may be applied directly to the outer surface or skin of the patient and may be disposed beneath an outer garment, wherein the mounting or removable securement to the patient may occur while the patient is standing, sitting or lying down, immediately after the surgical procedure. The versatility of such a preferred and proposed compression garment allows its use for relatively brief periods such as forty-eight hours post surgical procedure or as long as thirty days thereafter.

SUMMARY OF THE INVENTION

The present invention is directed to a compression garment used for post operative patients having been involved in any of a wide variety of body sculpting surgical procedures and including, but not limited to lipoplasty. Further, the compression garment assembly of the present invention is structured to overcome various problems and disadvantages associated with conventional or known post operative devices intended to apply some type of retaining or compressive force to surgically affected areas of a post operative patient. Accordingly, the structural and operative features of the compression garment of the present invention will serve to reduce pain and recovery time, by diminishing the swelling associated with the surgical procedure. In addition proper use and application of the compression garment assembly of the present invention will prevent the appearances of bruises conventionally associated with high pressure related complications when utilizing known or conventional devices of the type generally set forth above. The application of the compression garment of the present invention in a correct operative position will result in elimination of abrasions or skin necrosis. Moreover, the application of an appropriate compressive force to the surgically affected areas of the post operative patient can be maintained for any appropriate time period depending upon the specific type of body contouring surgery involved.

More specifically, the compression garment of the present invention includes a base or core formed of a flexible, compressible material such as, but not limited to, an economically, cost effective foam material. Such a preferred foam material from which the base is formed may include polystyrene foam which is relatively inexpensive. Such a foam material is adapted to accommodate varying degrees of compression to the bony prominences and the soft tissue through the application of lesser or greater amounts of compressive forces as appropriate.

In addition, a cover assembly is disposed in overlying covering relation to the flexible and compressible material base or core. As such, the cover assembly may include a first cover member disposed in overlying, covering relation to an internal face surface of the core and which is disposed to come in to direct contact with the skin of the patient. In addition, the covering assembly may include a second cover member extending in overlying, covering relation to the outer surface of the foam material base. Variations in the structural features of the covering assembly, specifically including the first and second cover members, may include their formation from cotton or other appropriate, natural or synthetic material. Such material(s) should also be non-allergenic and/or otherwise structured to prevent complications when maintained in confronting engagement with the skin of the post operative patient for extended periods. Further, the first and second cover members may include an integral or otherwise fixedly attached interconnecting structure or may comprise a one piece structure disposed in substantially enclosing relation to the inner and outer surfaces of the base, as well as the contiguously disposed peripheral portions or junctions thereof.

It is to be understood that the compression garment of the present invention may be manufactured and provided in various sizes to accommodate different individuals. In addition, the various preferred embodiments of the subject compression garment include a closure assembly which is preferably disposed at each of the opposite ends of the base. The closure assembly is structured to removably retain the base or core in a closed orientation while in an operative position, applying appropriate compressive force to the surgically affected areas of the patient's body. As will be described in greater detail hereinafter, the closed orientation may be defined in at least some of the preferred embodiments of the present invention as surrounding a majority or entirety of the torso of the patient, wherein the opposite ends are brought into a substantial or predetermined alignment with one another. Such an aligned relation of the opposite ends may comprise a variable overlapping disposition to one another. As such, an appropriate compressive force may be applied to the torso or other appropriate portion of the user's body depending on the size and shape of the engaged body portion. Further, the substantially aligned relation of the opposite ends may include a substantially adjacent or contiguous positioning of the opposite ends when in the closed orientation. Alternatively, the substantially aligned relation of the opposite ends may comprise an at least minimal spacing from one another, while still in the closed orientation and surrounding relation to the torso or other affected portions of the patient's body.

Accordingly, application of the compression garment of the present invention to a post operative patient in an operative position comprises a closed orientation thereof, wherein the base effectively surrounds the affected portions of the patient's body specifically including, but not limited to, the torso portion. The structural and operative features of the garment assembly facilitates a compressive force being applied in a manner which will accommodate the bony prominences of the body, through the application an appropriately lesser compressive force, while concurrently or simultaneously applying an appropriately greater compressive force to the soft tissue portions. As a result, the compression garment of the present invention will serve to reduce pain and recovery time by diminishing swelling in a post operative patient while preventing the occurrence of bruises or other skin abrasions. Moreover, the accumulation of fluids or the avoidance of seromas and hematomas will be accomplished while maintaining appropriate venous and lymphatic circulation.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a perspective view of one preferred embodiment of the compression garment of the present invention represented in a closed orientation which would be assumed when the compression garment is in an operative position on a patient.

FIG. 2 is a front view of the embodiment of FIG. 1 in an open orientation.

FIG. 3 is a sectional view along line 3-3 of FIG. 2.

Like reference numerals refer to like parts throughout the several views of the drawings.

DETAILED DESCRIPTION OF THE PREFERRED EMBODIMENT

Figure 5:
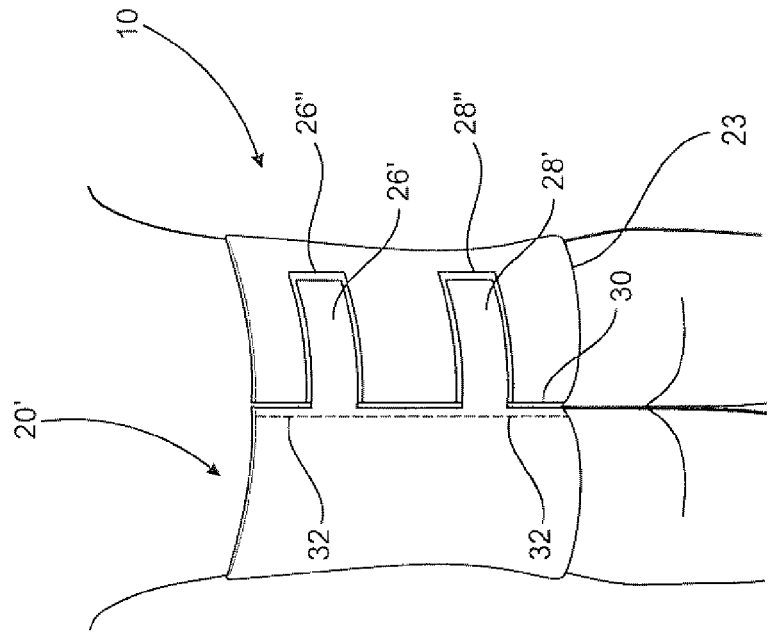
FIG. 5 is a rear perspective view showing details of a closure assembly associated with the embodiment of FIGS. 1 through 4.
Figure 4:
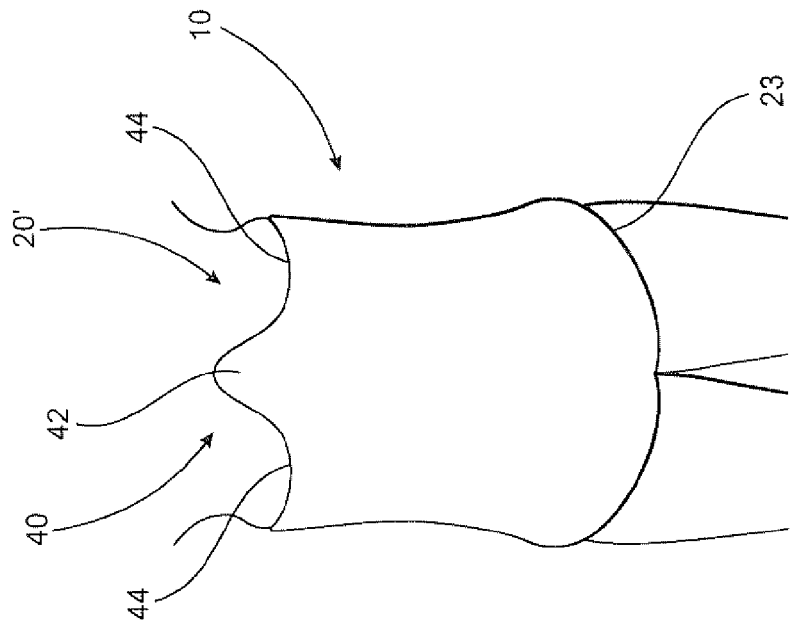
FIG. 4 is a front perspective view of yet another embodiment of the compression garment of the present invention disposed in an operative position and in a closed orientation on a female patient.

As represented in the accompanying Figures, the present invention is directed to a compression garment generally indicated as 10 which is selectively disposable between a closed orientation as represented in FIGS. 1, 4 and 5 and an open orientation as represented in FIG. 2. The compression garment 10 includes structural and operative features which facilitate its use in the treatment of post operative patients involved in various type of body contouring surgery. In particular the compression garment 10 is structured to apply appropriate compressive forces to the surgically affected portion of the patient's body and in particular the torso portion as specifically represented in FIGS. 4 and 5.

In modern day surgical procedures, lipoplasty or other body contouring surgical procedures may affect the torso of a patient's body in generally a "360° range" in order to accomplish a more complete sculptured appearance. Therefore, the compressive forces applied to the patient on a post operative basis are preferably applied substantially to the entirety or at least a majority of the torso when the compression garment 10 is correctly disposed in an operative position.

As set forth above, the operative position is more specifically defined and/or comprises the disposition thereof in the closed orientation of FIGS. 1, 4 and 5, wherein the garment 10 substantially surrounds and forcible engages indicated portions of the torso. For purposes of clarity, the affected parts of the torso may include the area substantially adjacent or contiguous to the breast area of the patient and extending therefrom down to and over the hip area. As such, the compression garment 10 covers and/or overlies, as well compressively engages the rib cage and iliac crest of the patient, as represented in FIGS. 4 and 5.

More specific structural features of the embodiment of FIGS. 1-5 include a base or core generally indicated as 12 formed from a flexible, compressible material. The material from which the core or base 12 is formed is preferably polystyrene foam of sufficient flexibility and compressibility to apply the appropriate pressure to various portions, specifically including the torso, of the user's body. Compressive forces will thereby be applied to both the soft tissue portions to the abdomen or back area as well as to the bony prominences such as the rib cage, iliac crest, etc. Accordingly in order to avoid any abrasions, bruising, etc., the flexibility, resiliency, and/or compressibility of the core or base 12 will serve to apply a relatively lesser amount of compressive force to the bony prominences and a relatively greater compressive force or pressure to the soft tissue portions of the torso. As such, the compression garment 10 of the present invention when disposed in the operative orientation as represented in FIGS. 1, 4 and 5 and further when in the closed orientation as also represented in these Figures, will reduce post operative pain and serve to diminish swelling and the avoidance of fluid accumulation or "seroma".

Additional structural features include a cover assembly generally indicated as 14 comprising a first or inner cover member 16 and a second or outer cover member 18, respectively disposed in overlying, covering relation to the inner surface 12' and outer surface 12" of the core or base 12. As such, each of the first and second cover members 16 and 18 may be formed from a cotton based or other appropriate material. Such material should also have non-allergenic properties or be otherwise treated to facilitate compatibility with the skin of the patient. This is especially true when the compression garment 10 is worn by the patient for an excessive period of time of up to and including approximately thirty days. Further, the first and second cover members 16 and 18 may be of a one piece sleeve like construction disposed in totally enclosing relation to the base or core 12. Alternatively, the first and second cover member 16 and 18 may be connected at one or more locations such that even a first or upper peripheral portion and a second or lower peripheral portion 20 and 22, respectively of the base or core 12 are covered by the covering assembly 14.

Yet additional structural features of the embodiments of FIGS. 1-5 of the compression garment 10 include a closure assembly generally indicated as 24. The closure assembly 24 includes at least one, but more practically a plurality of elongated closure member pairs as at 26 and 28. Each of the closure member pairs 26 and 28 include elongated straps, belts or other structures defining the closure members 26', 26" and 28', 28". As clearly represented in FIG. 2, each of the elongated, closure member pairs 26 and 28 include one of the closure members 26' and 28' extending outwardly from one longitudinal end 30. The opposite, corresponding closure members 26" and 28" are mounted or affixed to the outer surface of the outer or second cover member 18 contiguous or adjacent to the other longitudinal end 32. As represented in FIG. 2 each of the closure members 26" and 28" are distinguishable from the outer surface of the second cover member 18 by not being a part thereof. Further, each of the closure members 26', 26" and 28', 28" of the closure member pairs 26 and 28 may be structured to accomplish a removable but secured connection with one another so as to maintain the compression garment 10 in the closed orientation of FIGS. 1, 4 and 5. Therefore each of the closure member pairs 26 and 28 may be formed from hook and loop type fasteners which facilitate the secure but easily separable connection of the closure member pairs 26 and 28 from one another.

As set forth above, when in the closed orientation and in the operative position substantially surrounding the torso of the patient, a compressive force is applied to the underlying portions of the user's body. Such compressive force may be at least partially varied or adjusted by positioning the closure member pairs 26 and 28 such that the opposite longitudinal ends 30 and 32 are brought into substantial alignment with one another. However, it is emphasized that the substantially aligned relation of the opposite ends 30 and 32, when the base 12 and/or compression garment 10 is in the closed orientation, comprises the opposite ends 30 and 32 being contiguously or adjacently disposed relative to one another or even disposed in a partially spaced relation to one another. Further the opposite ends 30 and 32 may be considered in substantial alignment with one another when they are at least partially and variably overlapping one another, as represented in phantom lines in FIG. 5. The degree of overlapping engagement between the ends 30 and 32 as well as the other positions of alignment will be dependent on the size and shape of the patient and will, at least to some extent, determine the amount of compressive force applied to the surrounded portion or torso of the patient. Obviously, the "tighter" the core or base 12 is disposed about and in confronting engagement with the torso of the patient, the greater the compressive force being applied to the torso. Therefore, the amount of compressive force applied to the patient may be considered to be variable in that elongated closure members 26', 26" and 28', 28" of the closure member pairs 26 and 28 may be variably positioned relative to one another so as to vary the overlapping engagement, and/or spacing of the opposite ends 30 and 32 relative to one another.

Yet additional structural features which at least partially distinguish the embodiment of FIGS. 1-3 from that of FIGS. 4 and 5 is the provision of an upper peripheral portion 20' having an at least partially "scalloped" configuration generally indicated as 40 and represented in FIG. 4. The scalloped configuration 40 is meant to accommodate and at least partially conform to the more pronounced breast area of a female patient. As such, the scalloped configuration 40 is disposed and configured to facilitate a comfortable fit while still maintaining the application of the preferred and appropriate compressive force to the torso of the patient, specifically to the area adjacent the breast portion of the female patient. More specific structural details of the scalloped configuration 40 as represented in FIG. 4 include an upwardly extending or protruding centrally disposed portion 42 located between spaced apart recessed portions 44, each disposed in substantially aligned relation with a different breast of the patient. As also set forth above, the embodiment of FIGS. 4 and 5 of the compression garment 10 respectively represent a front view and rear view thereof. As such, it is indicated that the scalloped configuration 40 applies more prominently to the frontal portion of the compression garment 10, wherein the first or upper peripheral portion 20' of the rear part of the compression garment 10 is substantially equivalent to the embodiment of FIGS. 1-3.

Accordingly the embodiments of FIGS. 4 and 5 are primarily, but not exclusively, directed for use by a female patient having a more prominent breast area In contrast, the embodiment of FIGS. 1-3 is primarily, but not exclusively, structured for use by a male patient, typically having a less prominent breast area. It is further emphasized that the primary difference between the embodiments of FIGS. 1-3 and the embodiment of FIGS. 4 and 5 is the aforementioned and described scalloped configuration 40 at the upper peripheral portion 20' of the core or base 12 and/or compression garment 10. For purposes of clarity, the upper peripheral portion 20, 20' is located substantially opposite to the lower peripheral portion 22 when the compression garment 10 is in the operative position on a patient as represented in FIGS. 4 and 5 concurrently to the core or base 12 being disposed in the closed orientation as represented in FIGS. 1, 4 and 5.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A compression garment for treating post operative patients, said compression garment comprising:
   a base including first and second peripheral portions, said base formed of a flexible, compressible material and disposable in an operative position on the patient,
   a first cover member extending in overlying, covering relation to an interior surface of the base,
   a second cover member extending in overlying, covering relation to an exterior surface of said base,
   a closure assembly attached to opposite ends of said base and structured to removably maintain said base in a closed orientation in said operative position,
   said base being dimensioned and configured to at least partially define said operative position as being in continuously surrounding relation to the torso and including said first peripheral portion disposed in substantially aligned relation to a breast area and said second peripheral portion disposed in substantially aligned relation to a hip area of the patient, and
   said first peripheral portion comprising a scalloped configuration comprising an upwardly extending centrally disposed portion and two recessed portions, each of said two recessed portions disposed in substantially aligned relation with a different breast of the patient.

2. A compression garment as recited in claim 1 wherein said closed orientation is at least partially defined by said closure assembly disposed in interconnecting, aligning relation to said opposite ends.

3. A compression garment as recited in claim 2 wherein said closure assembly and said base are cooperatively structured to vary said closed orientation; said closed orientation being variably dependent on the size of the patient.

4. A compression garment as recited in claim 3 wherein said aligning relation of said opposite ends comprises said opposite ends disposed in overlapping relation to one another.

5. A compression garment as recited in claim 4 wherein said closure assembly comprises a plurality of elongated closure member pairs, said plurality of closure member pairs disposed in spaced relation to one another along corresponding lengths of said opposite ends.

6. A compression garment as recited in claim 5 wherein one of said closure members of a corresponding one of said closure member pairs comprises a hook type fastener and the other of said closure members comprises a loop type fastener.

7. A compression garment as recited in claim 1 wherein said closure assembly comprises a plurality of elongated closure member pairs, said plurality of pairs disposed in spaced relation to one another along corresponding lengths of said opposite ends.

8. A compression garment as recited in claim 7 wherein said closed orientation is at least partially defined by said closure assembly disposed in interconnecting, aligning relation to said opposite ends; said aligning relation of said opposite ends comprising a variable overlapping relation of said opposite ends to one another.

9. A compression garment as recited in claim 1 wherein said closure assembly and said base are cooperatively structured to vary said closed orientation; said closed orientation being variably dependent on the size of the patient.

10. A compression garment as recited in claim 9 wherein said closed orientation is at least partially defined by said closure assembly disposed in interconnecting, aligning relation to said opposite ends; said aligning relation of said opposite ends comprising a variable overlapping relation of said opposite ends to one another.

11. A compression garment as recited in claim 10 wherein said operative position is further defined by said opposite ends disposed in said closed orientation and extending along a length of a back portion of the torso of the patient.

* * * * *